United States Patent [19]
Fayram et al.

[11] Patent Number: 5,814,082
[45] Date of Patent: Sep. 29, 1998

[54] LAYERED CAPACITOR WITH ALIGNMENT ELEMENTS FOR AN IMPLANTABLE CARDIAC DEFIBRILLATOR

[75] Inventors: Timothy A. Fayram, Gilroy; Benjamin D. Pless, Atherton, both of Calif.; Samuel Parler, Clemson, S.C.; William H. Elias; Scott McCall, both of Six Mile, S.C.

[73] Assignee: Pacesetter, Inc., Sunnyvale, Calif.

[21] Appl. No.: 841,542

[22] Filed: Apr. 23, 1997

[51] Int. Cl.[6] .............................. A61N 1/39; A61N 1/375
[52] U.S. Cl. .................. 607/5; 607/4; 361/301.4
[58] Field of Search .................. 607/5, 4; 361/301.4

[56] References Cited

U.S. PATENT DOCUMENTS

| | | |
|---|---|---|
| 4,771,362 | 9/1988 | Behn . |
| 5,131,388 | 7/1992 | Pless et al. . |
| 5,331,505 | 7/1994 | Wilheim . |
| 5,522,851 | 6/1996 | Fayram . |
| 5,550,705 | 8/1996 | Moncrieff . |
| 5,660,737 | 8/1997 | Elias et al. . |
| 5,749,911 | 5/1998 | Westlund . |

Primary Examiner—William E. Kamm
Assistant Examiner—Carl H. Layno
Attorney, Agent, or Firm—Steven M. Mitchell

[57] ABSTRACT

A capacitor for an implantable cardiac defibrillator with a housing defining a chamber. A plurality of flat, stacked, charge storing layers reside within the chamber. Each of the layers includes at least a first and a second electrically conductive sheets separated by a sheet in between. The first sheet is electrically connected to the housing, and the second sheet is electrically isolated from the housing. The layers each have a periphery having at least one alignment element, with the second sheet extending to the periphery along at least a portion of the alignment element, such that the layers may be engaged at the alignment element to register the layers during assembly.

26 Claims, 5 Drawing Sheets

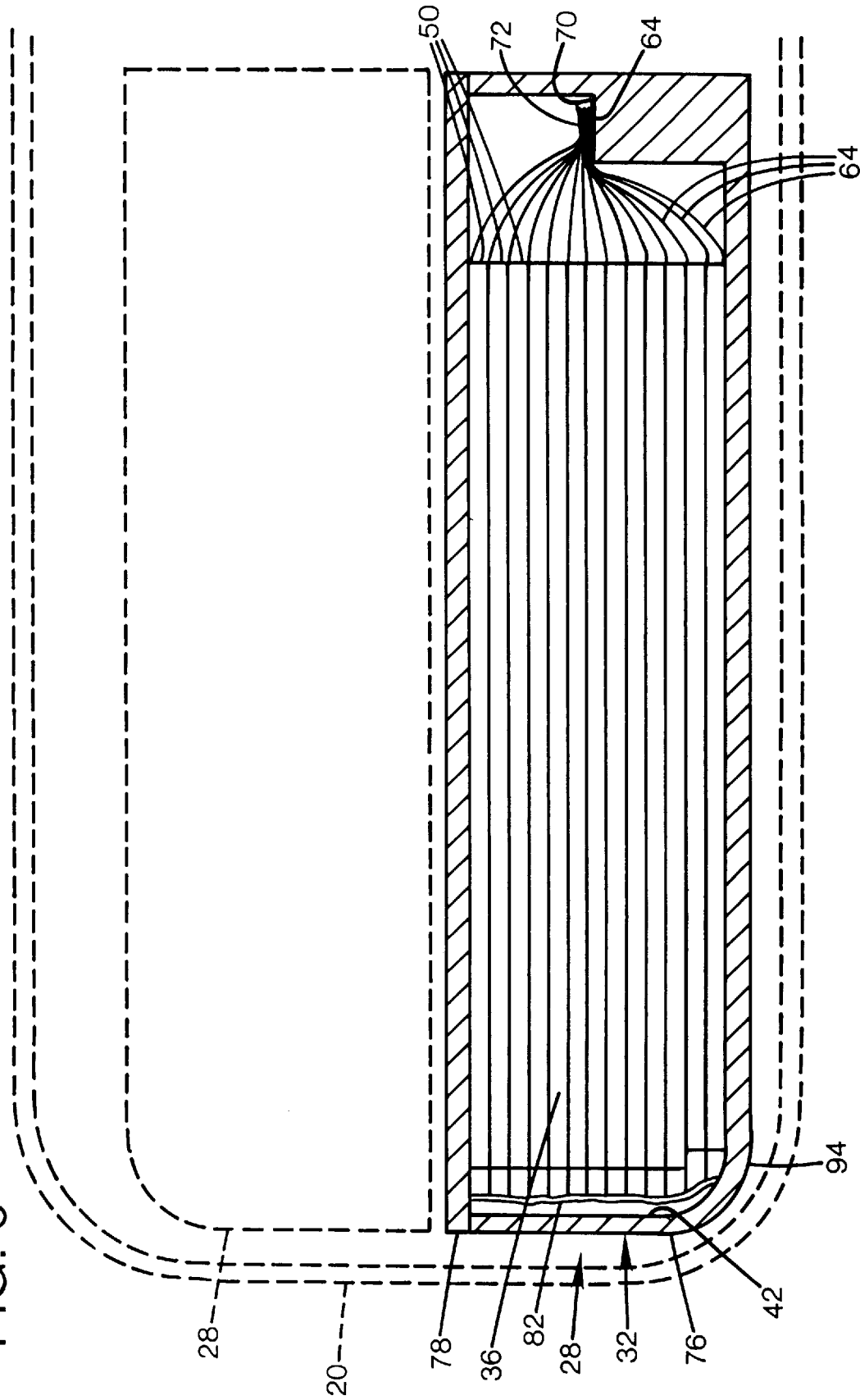

LAYERED CAPACITOR WITH ALIGNMENT ELEMENTS FOR AN IMPLANTABLE CARDIAC DEFIBRILLATOR

FIELD OF THE INVENTION

The invention relates to capacitors, and more particularly to capacitors for implantable cardiac defibrillators.

BACKGROUND AND SUMMARY OF THE INVENTION

Defibrillators are implanted in patients susceptible to cardiac arrhythmias or fibrillation. Such devices provide cardioversion or defibrillation by delivering a high voltage shock to the patient's heart, typically about 500–750V. High voltage capacitors are used in defibrillators to accumulate the high voltage charge following detection of a tachyarrhythmia. It is desirable to make implantable devices as small as possible, with slim, flat packages being desired for pectorally implanted defibrillators. Therefore, flat capacitors have been developed to avoid the disadvantages of traditional cylindrical aluminum electrolytic capacitors.

Such a flat capacitor is disclosed in U.S. Pat. No. 5,522,851 to Fayram, which is incorporated herein by reference. Flat capacitors include a plurality of layers laminarly arranged in a stack. Each layer includes an anode and a cathode, with the anodes and cathodes being commonly connected to respective connectors. The layers may be cut in nearly any shape, to fit within a similarly shaped housing designed for a particular application. The capacitance of such a device is proportional to the number of layers, and to the area of each layer, providing significant design flexibility. However, it is desirable to further improve the capacitance per unit volume ratio of current devices, which currently devote some volume to clearances for preventing shorting of components, and to fastening and alignment elements for securing the device components to each other.

The present invention overcomes the limitations of the prior art by providing a capacitor for an implantable cardiac defibrillator with a housing defining a chamber. A plurality of flat, stacked, charge storing layers reside within the chamber. Each of the layers includes at least a first and a second electrically conductive sheet separated from each other by a separator sheet in between. The first conductive sheet is electrically connected to the housing, and the second conductive sheet is electrically isolated from the housing. The layers each have a periphery having at least one alignment element, with the second sheet extending to the periphery along at least a portion of the alignment element, such that the layers may be engaged at the alignment element to register the layers by contacting the second sheets during assembly.

BRIEF DESCRIPTION OF THE DRAWINGS

FIG. 6 is a cross sectional side view of a single capacitor layer taken along line 6—6 of FIG. 2.

DETAILED DESCRIPTION OF A PREFERRED EMBODIMENT

Figure 1:
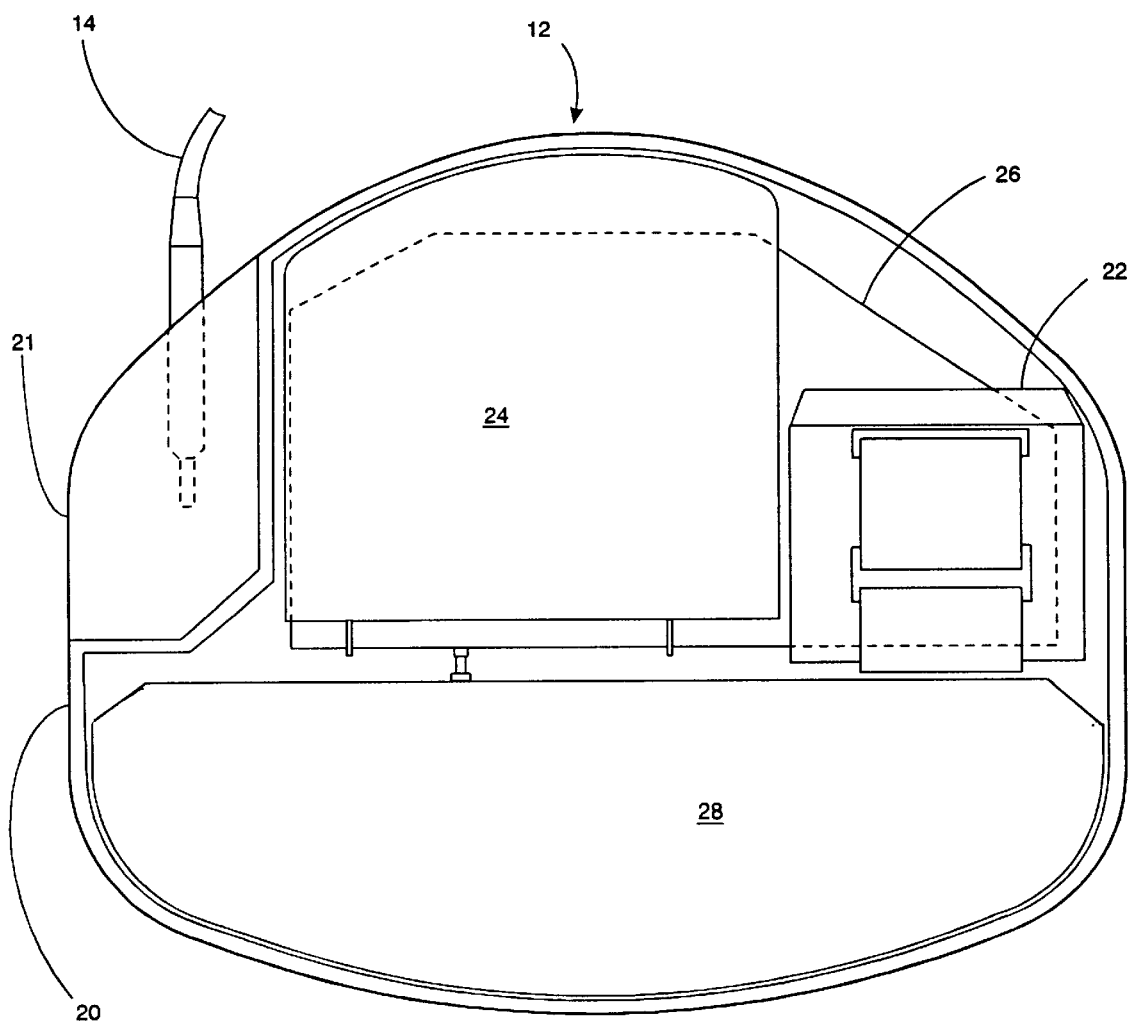
FIG. 1 shows an implantable defibrillator having capacitors according to the present invention.

FIG. 1 illustrates a defibrillator 12 for pectoral implantation. A single pass endocardial lead set 14 extends from the unit, through the patient's subclavian vein, and into the patient's heart. The defibrillator 12 includes an outer housing 20 that includes a connector portion or header 21 for attachment of the lead set 14. The housing 20 contains a transformer 22, a battery 24, printed circuit assembly 26, and a two capacitors 28 (only one shown.) The battery provides low voltage electrical energy that is converted by transformer 22 to charge the capacitor when needed so that they may provide a high voltage shock. The printed circuit assembly 26 connects to the lead set 14 so that it may sense and analyze electrical signals from the heart, and control the delivery of an appropriate therapy such as a high voltage shock.

Figure 2:
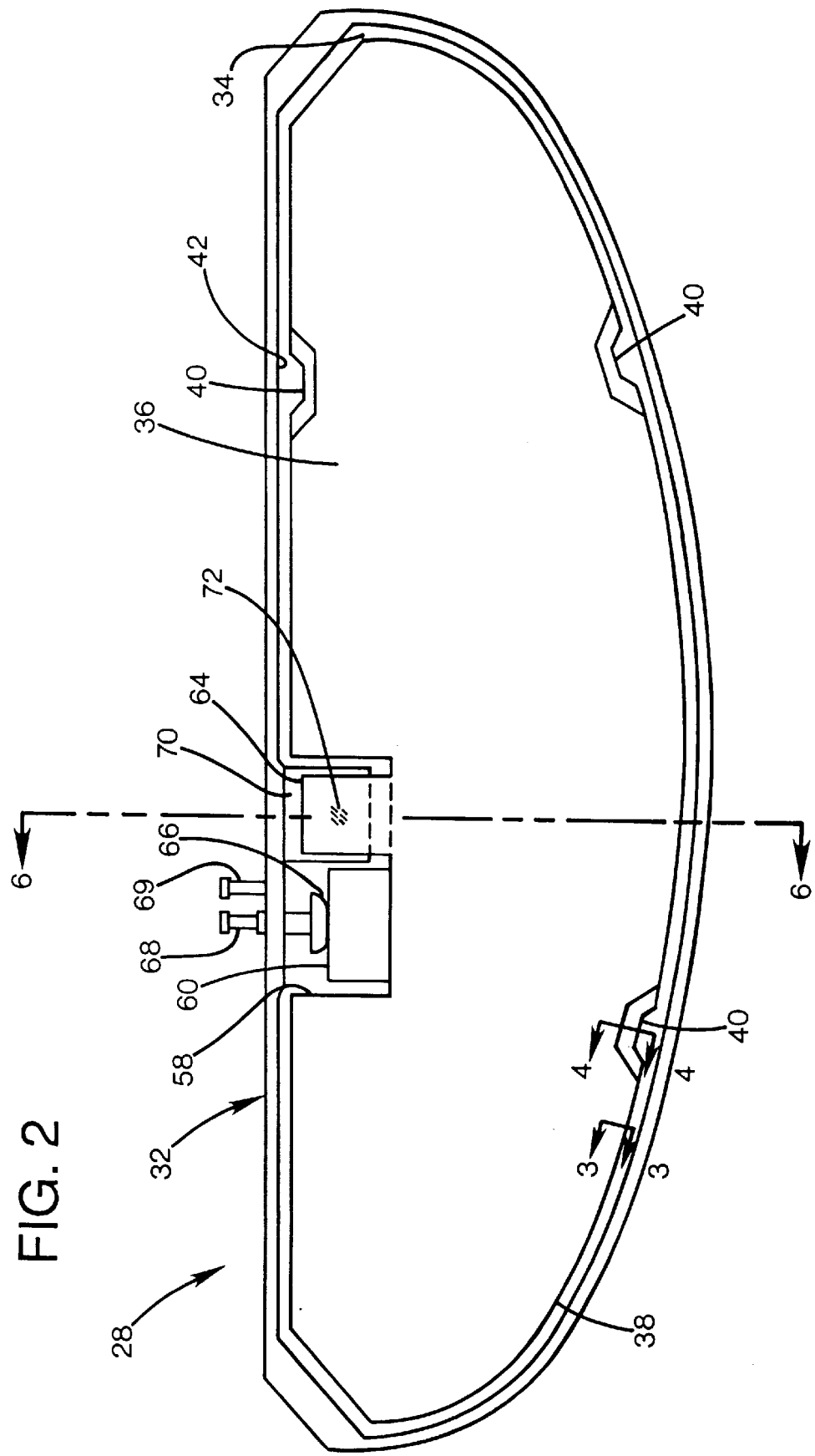
FIG. 2 is a plan view of the interior of the capacitor of FIG. 1.

FIG. 2 illustrates in detail the construction of the capacitor 28, which may be designed as virtually any flat shape to conform to a desired housing shape. The capacitor includes a metallic housing 32 defining a chamber 34, in which resides a capacitor stack 36. Housing 32 may alternatively be plastic. The capacitor stack has a periphery 38 that includes a cutout connection region 58 discussed below, and three small alignment elements or notches 40 that provide recesses spaced away from the interior surface 42 of the capacitor housing side wall. The remaining major portion of the periphery has gently curved convex portions, and straight portions. The overall periphery of the stack is defined as the edge of the layers or sheets that extend farthest at a particular location.

Figure 3:
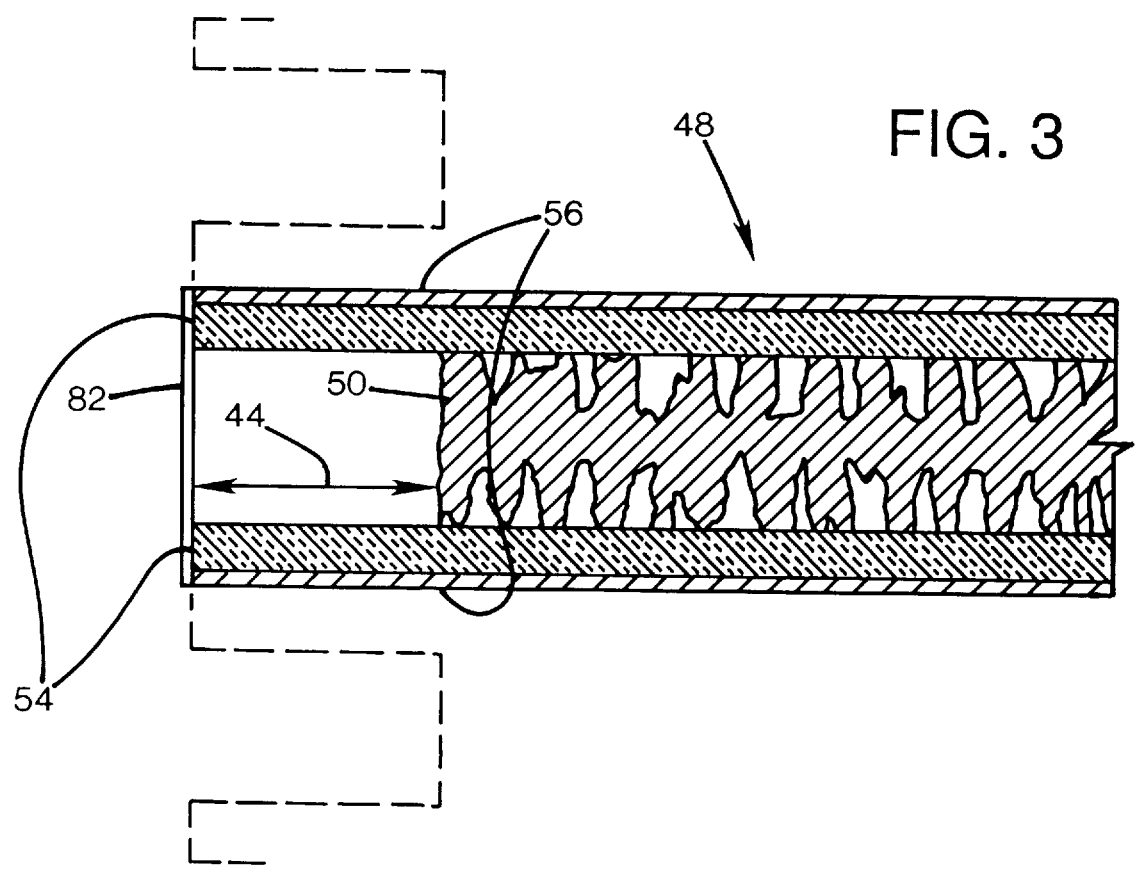
FIG. 3 is a cross sectional side view of a single capacitor layer taken along line 3—3 of FIG. 2.
Figure 4:
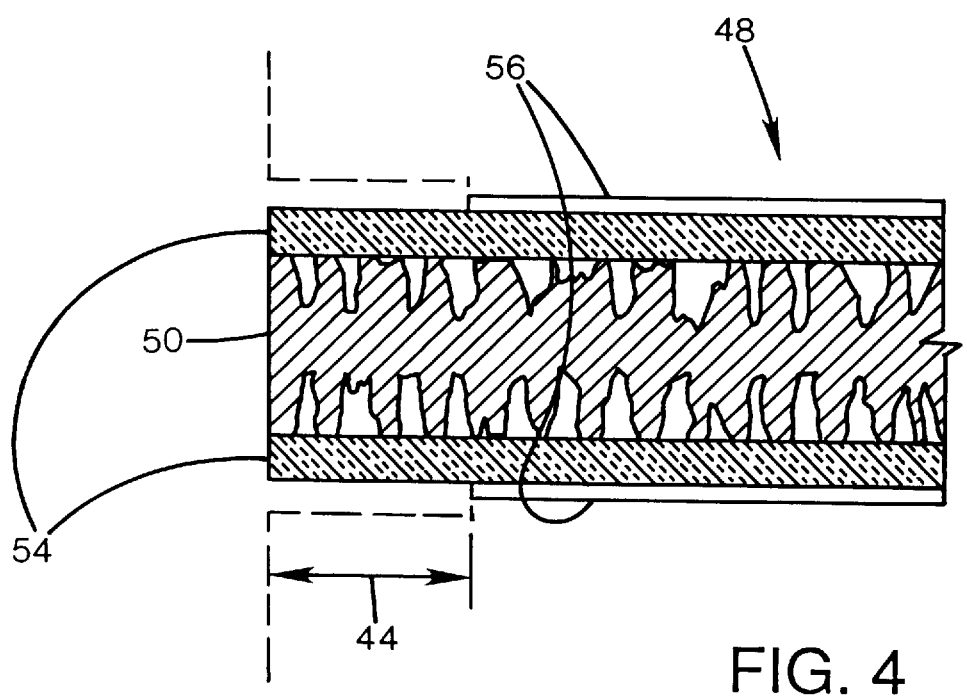
FIG. 4 is a cross sectional side view of a single capacitor layer at an alignment element, taken along line 4—4 of FIG. 2.

As shown in FIGS. 3 and 4, the capacitor stack 36 is formed of a number of essentially identical flat capacitor layers 48 whose electrical elements are connected in parallel. The number of layers determines the capacitance and thickness of the device; in the preferred embodiment, 13 layers are used. Each layer 48 is a sandwich of sheets: a central anode 50 that is highly etched on both major surfaces and a pair of separator sheets 54 (typically paper) covering a pair of aluminum cathode foil sheets 56 and positioned on the opposite sides of the anode. Only a single cathode foil sheet 56 is positioned between the separator sheets 54 in adjacent layers 48 of the capacitor stack 36. Thus, the sequence in the stack 36 is: anode sheet, separator sheet, cathode sheet, separator sheet, anode sheet, etc. In the preferred embodiment, the anode 50 consists of two sheets, each approximately 0.004 inch thick and stacked together. Single, double, triple and even higher multiples of anode sheets may be used. Each separator sheet is typically 0.002 inch thick, and each cathode sheet is 0.0008 inch thick. The separator sheet may be a single paper sheet or may comprise multiple sheets.

The etched anode layer can be "formed" by passing a current through the anode in the presence of an electrolyte. This generates an oxide layer that functions as a dielectric. The forming is typically done before assembly of the stack. Once the capacitor is assembled, an electrolyte is injected into the chamber through a hole in the housing which is then sealed.

As shown in FIG. 3, at the major portion of the stack periphery, the paper sheets 54 and cathode sheets 56 extend beyond the anode sheet 50 by a separation distance 44 to prevent contact between the cathode and anode due to any misalignment. The separation distance is preferably about 0.030 inch (0.75 mm) (but may be as small as 0.01 inch), which is sufficiently large to avoid contact, and is sufficiently small to avoid excessively reducing the capacitance of the device, as the extending portions of the cathode do not contribute to the device capacitance. To provide effective isolation, the separator layers 54 extend the full separation distance, so that the smallest distance between respective exposed conductive portions of the cathode and anode are separated by the full separation distance. The separating paper layers 54 also serve as a repository for the electrolyte between the anode and cathode layers.

Figure 5:
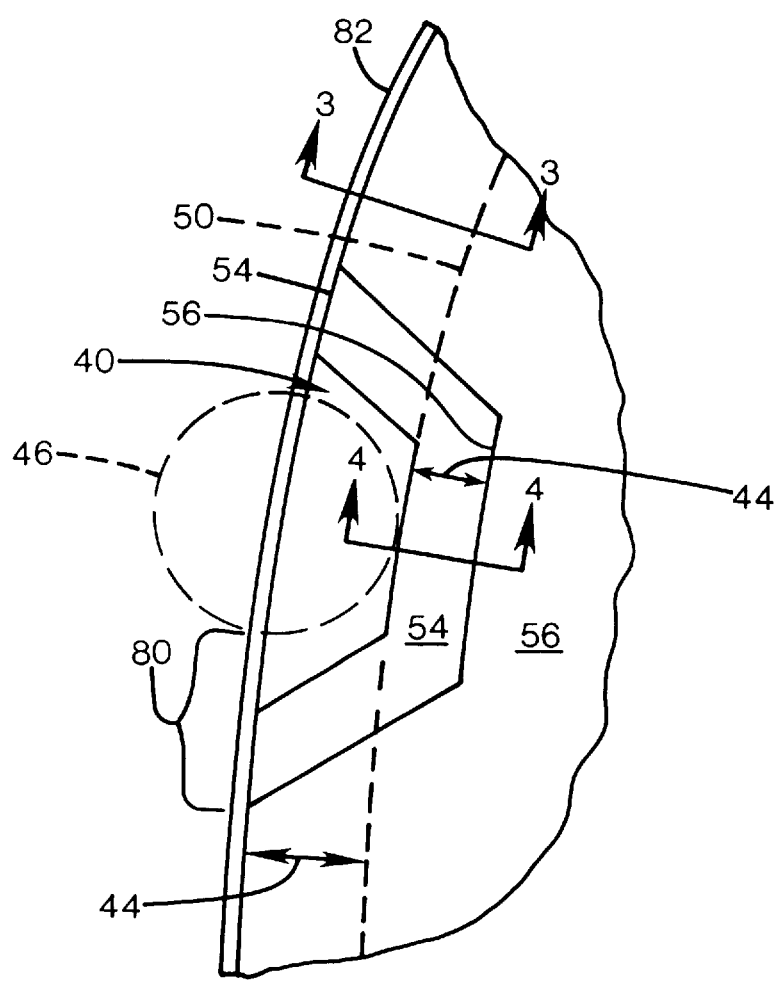
FIG. 5 is an enlarged plan view of a capacitor layer at an alignment element.

As shown in FIGS. 4 and 5, at an alignment element 40, the anode 50 extends to the periphery of the stack, along with paper sheets 54. The edge of the cathode sheet is spaced apart from the periphery by the separation amount 44. The paper extends to the same distance as the anode 50, so that it covers the anode surface. The paper does not extend beyond the anode at the alignment element so that the anode may be used for mechanical alignment during assembly to abut a boss 46 on an assembly.

As shown in FIG. 5, the cathode and anode edges are spaced apart by the separation amount 44 along the major portion of the periphery, where the cathode sheets extend farther, and within the alignment element, where the anode sheets extend farther. In these regions, the paper extends to the edge of the farther-extending sheet. However, there is a transitional region 80 in which the cathode edge crosses the anode edge and the respective edges are spaced apart by less than the separation amount. In the transitional region, the paper extends beyond both sheets 50 and 56. As shown, the paper extends by at least the separation amount from the edge of the less extended sheet when in the transitional region 80. At a minimum, the paper should extend sufficiently so that the sum of the distances from the edge of the paper to the edges of the respective conductive sheets is greater than or equal to the separation amount.

As shown in FIG. 2, each of the layers 48 has a cutout region 58 at its periphery, with the cutouts of each layer being aligned when the sheets are installed in the housing to provide space for electrical connections. The anodes 50 include anode tabs 60 extending into the cutout in registration with each other. Similarly, the cathodes 56 include cathode tabs 64 that extend into the cutout region and registered with each other, but spaced apart from the anode tabs by at least the separation amount to allow separate connection without contacting. The paper spacers 54 do not extend fully into the cutout, but extend only by at least the separation amount to prevent contacting. Therefore, the free ends of the cathodes, like the anodes, may be connected together in parallel when the tabs are brought together in a bundle.

A stack of layers is positioned in a fixture having a boss 46 corresponding to each alignment notch 40, with the layers being registered and constrained as each boss contacts an edge portion of each anode sheet as shown in FIG. 5. After all layers have been assembled into a stack, the stack is taped to provide mechanical stability. The anode tabs 60 are compressed together and welded together at their free ends, such as with a YAG laser. A tab of aluminum is welded to the anodes and to the anode pin.

The stack with anode tab and anode pin 68 is then installed in the housing. The anode pin 68 is electrically insulated from the housing. The cathode tabs 64 are electrically connected to the capacitor housing. A cathode lead 69 provides an external electrical connection to the housing. The cathode tabs 64 are ultrasonically welded to a housing step 70 abutting the periphery of the interior of the housing. As shown in FIG. 6, the step height is about half the height of the stack 36, so that the top and bottom cathode sheets need not be excessively deflected. An ultrasonic tool compresses the cathode tabs against the step at a weld point 72, and imparts ultrasonic energy to provide a secure electrical and mechanical connection.

As shown in FIG. 6, the housing 32 of the capacitor 28 includes a case 76, and a flat lid 78 overlaying the case and resting on the case's upper rim. The lid is attached and the housing sealed to prevent loss of electrolyte solution from the housing. This is achieved by laser welding the entire periphery of the lid while maintaining pressure on the lid.

In an alternative embodiment, the lid 78 may include alignment pins for registration with one or more of the alignment elements. These pins would preferably be of an insulative material. The alignment pins could alternatively be included on the case 76.

After aging and testing, two capacitors are installed in a single defibrillator unit. The capacitors are stacked with their lids facing toward the printed circuit. Because the defibrillator housing 20 has radiused edges for a physiologic shape appropriate to an implanted device, the capacitor housing has a 0.070 inch radiused edge 94 about a portion of its lower periphery. This permits a pair of capacitors to efficiently fill the defibrillator housing 20. So that the capacitor layers efficiently fill the capacitor housing, the lowest two layers may have reduced peripheries to avoid abutting the radius. The remaining layers extend closer to the housing wall to maximize capacitance for a given housing volume, with the preferred spacing being about 0.034 inch.

While the invention is described in terms of a preferred embodiment, the following claims are not intended to be so limited. For instance, the use of three alignment elements is not necessary, as the welding of the anode tabs serve to align the layers at one position, functioning as an alignment element. Only one other alignment element is required in addition to the tabs in a minimal configuration.

We claim:

1. An implantable cardiac defibrillator comprising:

an outer housing defining a chamber;

an energy source within the outer housing;

a capacitor within the housing;

the capacitor comprising a capacitor housing and a plurality of flat, stacked, charge storing layers within the chamber;

the layers each including at least first and second sheets separated from each other by a separator sheet positioned therebetween;

the layers each having a periphery; and the periphery of each layer having a minor portion comprising at least one alignment element, and wherein the second sheet extends beyond the first sheet at the alignment element.

2. The defibrillator of claim 1 wherein the alignment element comprises a notch recessed relative to the major portion of the periphery.

3. The defibrillator of claim 1 including at least three alignment elements.

4. The defibrillator of claim 3 wherein at least two of the alignment elements are widely spaced apart, such that engagement of the alignment elements minimizes angular disposition of the layers.

5. The defibrillator of claim 1 wherein the alignment elements are separated from the capacitor housing by a gap, such that the second sheet is spaced apart from the capacitor housing.

6. The defibrillator of claim 1 wherein the periphery includes a connection region wherein each of the first and second sheets has an extending tab for connection to an electrical element, and wherein the alignment element is separate from the connection region.

7. The defibrillator of claim 1 wherein each portion of the periphery comprises a configuration selected from a group of configurations comprising:
   a first configuration in which the first sheet extends beyond the second sheet by at least a preselected amount,
   a second configuration in which the second sheet extends beyond the first sheet by at least the preselected amount, and
   a third configuration in which the separator sheet extends beyond the first sheet by a first amount, the separator sheet extending beyond the second sheet by a second amount, the sum of the first amount and the second amount being at least the preselected amount.

8. The defibrillator of claim 7 wherein the preselected amount is at least 0.010 inch.

9. The defibrillator of claim 7 wherein in the first configuration the separator sheet is sized and positioned to extend by at least the preselected amount beyond the second sheet, and in the second configuration the separator sheet is sized and positioned to extend by at least the preselected amount beyond the first sheet.

10. The defibrillator of claim 7 wherein in the first configuration the separator sheet is sized and positioned to extend by the same amount as the first sheet, and in the second configuration the separator sheet is sized and positioned to extend by the same amount as the second sheet.

11. The defibrillator of claim 1 wherein the separator sheet is sized and positioned to extend to the periphery of the layer at the major portion of the periphery and at the alignment elements.

12. The defibrillator of claim 1 including a layer of separator film wrapped about the periphery wrapped about the layers, such that the peripheries of layers do not contact the capacitor housing.

13. The defibrillator of claim 1 wherein the outer housing comprises an electrically conductive material.

14. A capacitor for an implantable cardiac defibrillator comprising:
   a housing defining a chamber;
   a plurality of flat, stacked, charge storing layers within the chamber;
   the layers each including at least first and second electrically conductive sheets electrically isolated from each other by a separator sheet positioned therebetween;
   each of the second sheets being electrically isolated from the housing; and
   the layers each having a periphery defining at least one alignment element, the second sheet extending to the periphery along at least a portion of the alignment element, such that the layers are engaged at the alignment element to register the second sheets.

15. The capacitor of claim 14 wherein the second sheet comprises a metal sheet having a thickness such that the second sheet resists buckling when a moderate force sufficient to slide one of the layers into alignment relative to at least another layer is applied to an edge of the second sheet.

16. The capacitor of claim 14 wherein the first sheet is sized and positioned to extend beyond the second sheet about a major portion of the periphery.

17. The defibrillator of claim 14 including at least three alignment elements.

18. The defibrillator of claim 17 wherein at least two of the alignment elements are widely spaced apart, such that engagement of the alignment elements minimizes angular disposition of the layers.

19. The defibrillator of claim 14 wherein the housing comprises an electrically conductive material.

20. The defibrillator of claim 19 wherein each of the first sheets has an electrical connection with the housing.

21. The defibrillator of claim 14 wherein each portion of the periphery comprises a configuration selected from a group of configurations comprising:
   a first configuration in which the first sheet extends beyond the second sheet by at least a preselected amount,
   a second configuration in which the second sheet extends beyond the first sheet by at least the preselected amount; and
   a third configuration in which the separator sheet extends beyond the first sheet by a first amount, the separator sheet extending beyond the second sheet by a second amount, the sum of the first amount and the second amount being at least the preselected amount.

22. The defibrillator of claim 21 wherein the preselected amount is at least 0.010 inch.

23. The defibrillator of claim 21 wherein in the first configuration the separator sheet is sized and positioned to extend by at least the preselected amount beyond the second sheet, and in the second configuration the separator sheet is sized and positioned to extend by at least the preselected amount beyond the first sheet.

24. The defibrillator of claim 21 wherein in the first configuration the separator sheet is sized and positioned to extend by the same amount as the first sheet, and in the second configuration the separator sheet is sized and positioned to extend by the same amount as the second sheet.

25. The defibrillator of claim 14 wherein the separator sheet extends to the periphery of the layer at the major portion of the periphery and at the alignment elements.

26. The defibrillator of claim 14 including a layer of separator film wrapped about the periphery wrapped about the layers, such that the peripheries of layers do not contact the capacitor housing.

* * * * *